United States Patent
Colinet et al.

(10) Patent No.: US 12,163,935 B2
(45) Date of Patent: Dec. 10, 2024

(54) METHOD FOR ANALYSING HYDROCARBONS

(71) Applicants: APIX ANALYTICS, Grenoble (FR); TOTAL SA, Courbevoie (FR)

(72) Inventors: Eric Colinet, Saint-Ismier (FR); Philippe Andreucci, Coublevie (FR); Pierre Puget, Saint-Ismier (FR); Matthieu Loriau, Lons (FR); John Richard Ordonez Varela, Lescar (FR); Frank Haeseler, Idron (FR)

(73) Assignee: TOTALENERGIES ONETECH, Courbevoie (FR)

( * ) Notice: Subject to any disclaimer, the term of this patent is extended or adjusted under 35 U.S.C. 154(b) by 934 days.

(21) Appl. No.: 16/970,988

(22) PCT Filed: Feb. 15, 2019

(86) PCT No.: PCT/FR2019/050354
§ 371 (c)(1),
(2) Date: Aug. 19, 2020

(87) PCT Pub. No.: WO2019/158879
PCT Pub. Date: Aug. 22, 2019

(65) Prior Publication Data
US 2020/0400626 A1    Dec. 24, 2020

(30) Foreign Application Priority Data
Feb. 19, 2018   (FR) .................................. 1851416

(51) Int. Cl.
*G01N 30/76* (2006.01)
*E21B 49/08* (2006.01)
(Continued)

(52) U.S. Cl.
CPC ......... *G01N 30/76* (2013.01); *E21B 49/0875* (2020.05); *G01N 30/30* (2013.01);
(Continued)

(58) Field of Classification Search
CPC ........ G01N 30/76; G01N 30/30; G01N 30/60; G01N 30/66; G01N 30/78; G01N 30/86;
(Continued)

(56) References Cited

U.S. PATENT DOCUMENTS 9,841,408 B2 * 12/2017 Puget ................. G01N 30/6052
10,216,698 B2 * 2/2019 Ernst ................... B81C 1/00238
(Continued)

FOREIGN PATENT DOCUMENTS

EP    3185011 A1    6/2017

OTHER PUBLICATIONS

Sobrado et al. Analytical Chemistry, vol. 92, Nov. 24, 2020, pp. 15845-15853.*

(Continued)

*Primary Examiner* — Maureen Wallenhorst
(74) *Attorney, Agent, or Firm* — Thomas | Horstemeyer, LLP

(57) ABSTRACT

The invention relates to a method for analysing hydrocarbons, with the implementation of a gas chromatography separation according to a first controlled temperature profile, to separate a sample into a plurality of analytes and the detection of at least one of said analytes by measurement of a variation of the resonance frequency of at least one resonator of nano-electromechanical system (NEMS) type covered with a functional layer made to vibrate at the resonance frequency thereof, under the effect of an adsorption or desorption of the analyte by the functional layer, the resonator being subjected to a second controlled temperature profile, lower than the first profile.

20 Claims, 11 Drawing Sheets

(51) Int. Cl.
*G01N 30/30* (2006.01)
*G01N 30/60* (2006.01)
*G01N 30/66* (2006.01)
*G01N 30/78* (2006.01)
*G01N 30/86* (2006.01)
*G01N 33/18* (2006.01)
*G01N 33/28* (2006.01)
*G01N 30/02* (2006.01)

(52) U.S. Cl.
CPC ............. *G01N 30/60* (2013.01); *G01N 30/66* (2013.01); *G01N 30/78* (2013.01); *G01N 30/86* (2013.01); *G01N 33/1833* (2013.01); *G01N 33/2823* (2013.01); *G01N 2030/025* (2013.01); *G01N 2030/765* (2013.01)

(58) Field of Classification Search
CPC ............... G01N 30/62; G01N 33/1833; G01N 33/2823; G01N 2030/025; G01N 2030/765; G01N 2030/3007; G01N 2030/3038; G01N 2030/3076; G01N 2030/3084; G01N 2030/625; G01N 2291/021; G01N 2291/0255; G01N 2291/0256; G01N 2291/0427; G01N 29/022; G01N 29/036; E21B 49/0875; Y10T 436/21; Y10T 436/25875
USPC ............. 436/25, 29, 30, 139, 161, 147, 181; 422/83, 89
See application file for complete search history.

(56) References Cited

U.S. PATENT DOCUMENTS

| | | |
|---|---|---|
| 2011/0011157 A1 | 1/2011 | Bourlon et al. |
| 2013/0125621 A1* | 5/2013 | Puget .................. G01N 30/463 73/23.39 |
| 2014/0026637 A1* | 1/2014 | Blanc ................. G01N 30/6095 73/23.39 |
| 2015/0020575 A1 | 1/2015 | Puget et al. |
| 2015/0308990 A1 | 10/2015 | Andreucci et al. |
| 2017/0184556 A1* | 6/2017 | Toffoli ............... G01N 33/0059 |
| 2018/0024100 A1* | 1/2018 | Sun ........................ G01N 30/76 73/23.4 |

OTHER PUBLICATIONS

Mo Li, et al., "Nanoelectromechanical Resonator Arrays for Ultrafast, Gas-Phase Chromatographic Chemical Analysis", Nano Letters, vol. 10, No. 10, Oct. 13, 2010, pp. 3899-3903.

J. Arcamone, et al., VLSI Silicon Multi-Gas Analyzer Coupling Gas Chromatographic and NEMS Detectors, 2011 International Electron Devices Meeting, vol. 1, 17, Jan. 16, 2012, pp. 29.3.1-29.3.4.

Search Report from co-pending, related PCT Application No. PCT/FR2019/050354, mailed Apr. 29, 2019.

Performance Evaluation of Gas Chromatography-Surface Acoustic Wave Fast Analytical Instrument, ZHU, Zuo-gang et al., Journal of Analytical Science, vol. 26, Issue 3, pp. 338-340.

Chinese Office Action in related Chinese Application No. 201980014105.3, mailed Nov. 29, 2022.

* cited by examiner

METHOD FOR ANALYSING HYDROCARBONS

FIELD OF THE INVENTION

The present invention relates to a method for analysing hydrocarbons in liquid or gaseous form.

PRIOR ART

A measurement chain for a gas chromatography analysis of hydrocarbons comprises an injector (gas valve or liquid injector type), a separation column, and at least one detector.

For the needs of the analysis, it is necessary to control at all points the temperature of the measurement chain.

In particular, a widely accepted dimensioning rule is to maintain the temperature of the injector and the detector at a constant value set at around 50° C. above the boiling point of the gaseous sample to analyse (the boiling point being the temperature above which the sample is in the gaseous state).

As regards the column, its temperature control is more subtle. Indeed, the temperature of the column must be adjusted in such a way as to ensure good separation of the different gas peaks constituting the sample to analyse while favouring good analysis speed. It is preferable to work at a column temperature comprised between the dew point and the boiling point of the sample.

Thus, it is very often necessary to maintain the column over a wide temperature range comprised between 20° C. and 350° C.

Two types of analyses are widely implemented. The first controls the temperature of the column at a constant value. This isothermal analysis is particularly well suited for simple gaseous samples at atmospheric pressure (small difference in the boiling points of the analytes constituting the sample) where the analysis cycle (time interval between 2 successive analyses) must be reduced to its strict minimum. The second approach by "temperature programming" resorts to linear temperature ramps consisting in raising progressively and by stages the temperature of the column. This second approach is used for complex samples having a significant difference of the different boiling points: for example complex mixtures which are in the liquid state at room temperature may be cited. The temperature ramps (rate of temperature rise expressed in ° C./min) are adjusted according to the separation capacity or analysis time needs. These ramps also make it possible to control absorption/desorption phenomena between the stationary phase (chemical substance functionalising the column) and the mobile phase (gas) in the column. It is this sharing between the stationary phase and the mobile phase that determines the speed of transit of a given analyte and thus makes it possible to separate two different analytes present in the sample to analyse.

The detector situated at the outlet of the column makes it possible to detect the different molecules and to convert them into chromatographic peaks thus separated.

Different detector technologies exist.

Detectors traditionally employed include catharometers (TCDs, acronym for Thermal Conductivity Detectors). An advantage of such a sensor is that it is universal, that is to say capable of detecting any type of gas. Another advantage is that this sensor does not destroy the gaseous compounds of the sample; it may thus be coupled in series with another type of detector. Finally, this detector is compatible with inert vector gases (helium, argon, nitrogen), even if its sensitivity is linked to the vector gas used. A drawback of this detector is that its sensitivity is of the order of a ppm for light compounds (carbon chains with fewer than 7 carbon atoms) and ten or so ppm for heavier compounds (carbon chains with more than 7 carbon atoms) for the best detectors currently available on the market.

Another type of sensor is called FID (Flame Ionisation Detector). Such a sensor has good sensitivity (less than a ppm) vis-à-vis hydrocarbons; furthermore, this sensitivity increases linearly with the number of carbon atoms. However, this detector is only sensitive to carbon containing products (alkanes, alkenes, aromatics) and is thus not universal. Furthermore, its operation requires a hydrogen flame which implies an important consumption of $H_2$ and which makes it not very compatible with explosive environments. Finally, this detector has the drawback of burning the gaseous compounds forming the sample.

Other types of detectors exist that are used in a more confidential manner for specific needs. Among these may be cited:

PFPDs (Pulse Flame Photonic Detectors) which have great sensitivity to sulphur or phosphorus containing products but which are not universal, involve the use of hydrogen and destroy the sample;

HIDs (Helium Ionisation Detectors) which are universal detectors with a detection limit of the order of a ppm and which are sensitive to the mass of the analyte, but which necessitate a radioactive source and which involve large consumption of helium; another drawback of these detectors is that they destroy a part of the sample;

NEMS (Nano-Electro-Mechanical-System) type detectors enable mass measurements based on a variation of the resonance frequency of a resonator under the effect of the adsorption or the desorption of an analyte on a functional layer deposited on the resonator. These detectors have great sensitivity (less than a ppm) over a wide range of C1 to C40 molecules (not limited to carbon chains). Being non-destructive of the sample, they may be coupled in series with another detector. Finally, these detectors are compatible with inert vector gases (helium, argon, nitrogen) without notable impact on sensitivity and with hydrogen (unlike HIDs). On the other hand, they are not very sensitive to light compounds (C1-C6).

For all of these detectors with the exception of NEMS, the operating temperature must be controlled above the boiling point of the gaseous sample to analyse in order to ensure the correct transport of the sample up to the sensitive part of the detector and the correct operation of the detector.

For NEMS detectors, the temperature must be finely controlled to optimise the detection limit thereof. Indeed, in so far as adsorption phenomena are minimised with increase in temperature, it is generally sought to maintain the detector at a sufficiently low temperature. However, if the temperature of the detector is lowered too much, the adsorption reaction is favoured to excess, which can lead to a condensation of the analyte on the resonator.

DESCRIPTION OF THE INVENTION

An aim of the invention is to design a method that can be implemented in a hazardous environment and having a good sensitivity for a wide range of hydrocarbons.

For this purpose, the invention proposes a method for analysing hydrocarbons, comprising:

the implementation of a gas chromatography separation according to a first controlled temperature profile, to separate a sample containing said hydrocarbon into a plurality of analytes;

the detection of at least one of said analytes by measurement of a variation of the resonance frequency of at least one resonator of nano-electromechanical system (NEMS) type covered with a functional layer made to vibrate at the resonance frequency thereof, under the effect of an adsorption or desorption of the analyte by the functional layer, said method being characterised in that the resonator is subjected to a second controlled temperature profile, lower than the first profile.

"Second profile lower than the first profile" is taken to mean that at each instant the temperature applied to the resonator is lower than the temperature applied to the chromatography column within which the separation is carried out.

In a particularly advantageous manner, the temperature difference between the first profile and the second profile is comprised between 5 and 150° C., preferably between 30 and 100° C., in an even more preferred manner between 40 and 60° C.

According to a preferred embodiment, the temperature of the first profile evolves between 50 and 400° C. The temperature of the second profile evolves for its part between 0 and 350° C.

According to an embodiment, the detection of at least one of said analytes further comprises the measurement of a variation of the resonance amplitude of the resonator.

In a particularly advantageous manner, the sample comprises carbon chains having between 16 and 40 carbon atoms.

For the implementation of said method, the resonator is advantageously encapsulated in a temperature regulated chamber, said chamber comprising a temperature regulating unit configured to make the temperature vary inside the chamber according to the predefined temperature profile.

Furthermore, the chromatography column may be encapsulated in a chamber thermally decoupled from the chamber in which the resonator is encapsulated.

According to an embodiment, the method further comprises an analysis of said at least one analyte by a catharometer arranged in a same fluidic conduit as the resonator.

In a particularly advantageous manner, the method may comprise the implementation of a processing to subtract from the base line of the response of the resonator the base line of a response of the resonator, called blank response, measured beforehand in the absence of circulation of a fluid for a same temperature profile.

Alternatively, the method may comprise the implementation of a measurement of the variation of the resonance frequency of at least one second resonator, called reference resonator, subjected to the same temperature profile but not exposed to the analyte, and the implementation of a processing configured to subtract from the response signal of the resonator exposed to the analyte the response signal of the reference resonator.

In a particularly advantageous manner, the molecular composition of the analyte is deduced from the measurement of the variation of the resonance frequency of the resonator.

Furthermore, when the variation of the resonance amplitude of the resonator has been measured, a fluidic characteristic of the analyte is deduced from said measurement.

One application of the invention is the comparison of two petroleum fractions, by implementing the method described above to analyse the composition of each of said fractions.

Another application of the invention is the assay of a determined compound in a hydrocarbon, wherein the method described above is implemented to detect said compound within a sample of hydrocarbon.

Another application of the invention is the assay of a determined hydrocarbon in water, wherein the method described above is implemented to detect said hydrocarbon within a sample of water.

The invention also relates to a drilling tool or an autonomous vehicle for the exploitation of hydrocarbons and/or underwater exploration, comprising an analysis system for the implementation of the method described above, said system comprising:

a gas chromatography column, arranged in a first temperature controlled chamber, a resonator of nano-electromechanical system type arranged in a fluidic conduit at the outlet of the chromatography column, said resonator comprising a functional layer and being arranged in a second temperature controlled chamber, a reading device suited to make the resonator vibrate at the resonance frequency thereof and to measure a variation of said resonance frequency under the effect of the adsorption or the desorption of the analyte by the functional layer, the first and the second chamber being thermally decoupled from each other, each chamber comprising a temperature regulating unit, said regulating units being configured to make the temperature vary in their respective chambers according to different profiles.

In a particularly advantageous manner, the analysis system further comprises a catharometer arranged in the fluidic conduit, upstream or downstream of the resonator.

BRIEF DESCRIPTION OF THE FIGURES

Other advantages and characteristics of the invention will become clear from the detailed description that follows, with reference to the appended drawings in which.

Figure 5:
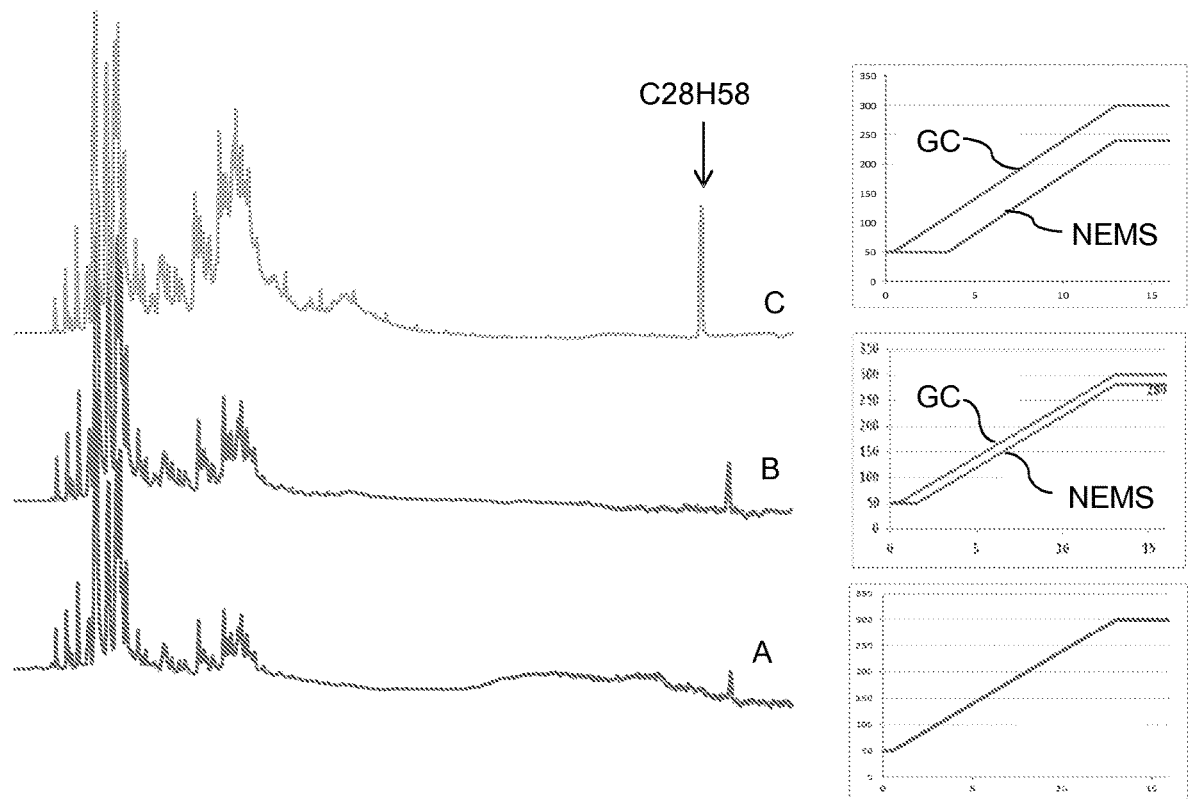
Figure 6:
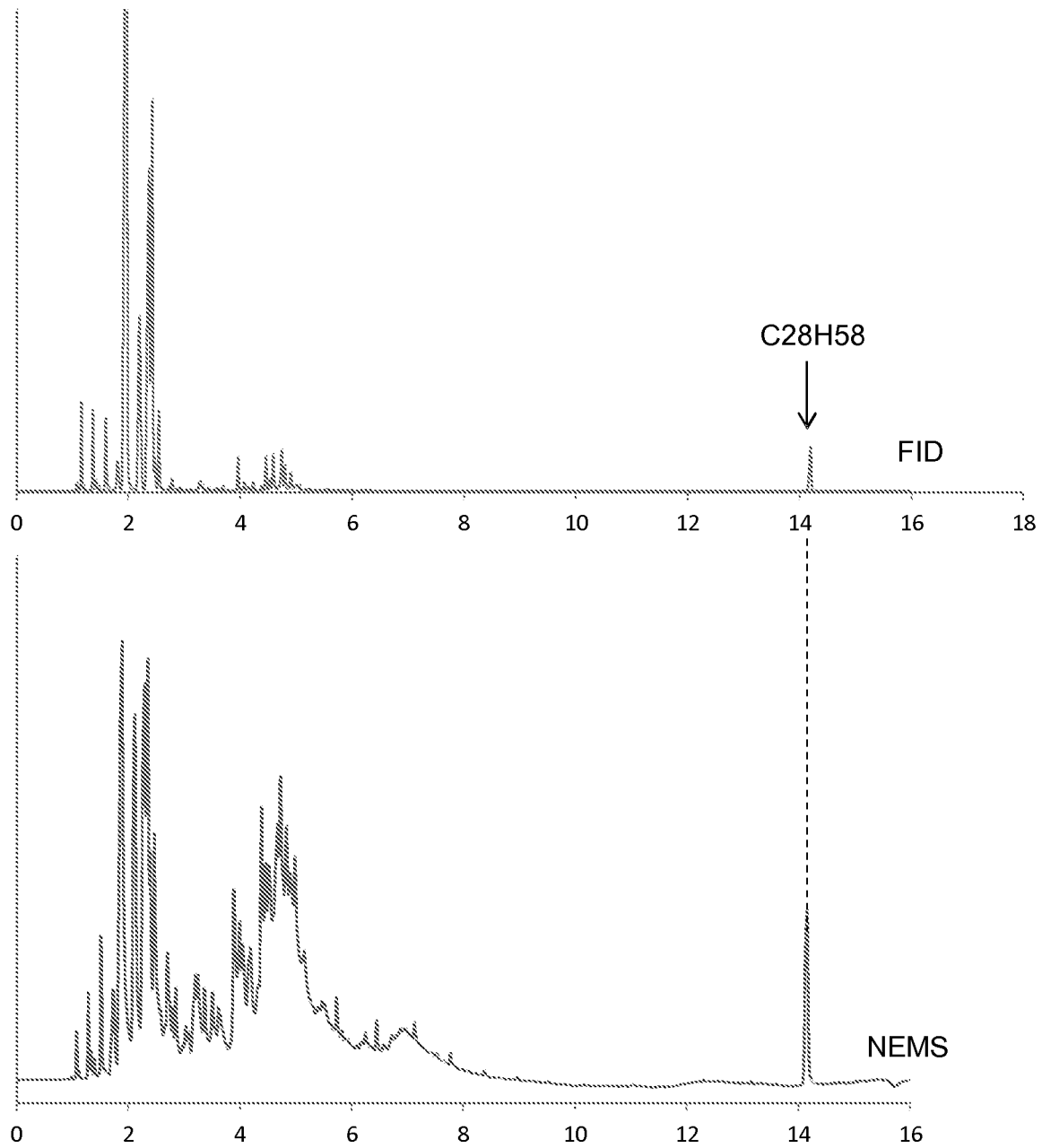
Figure 7:
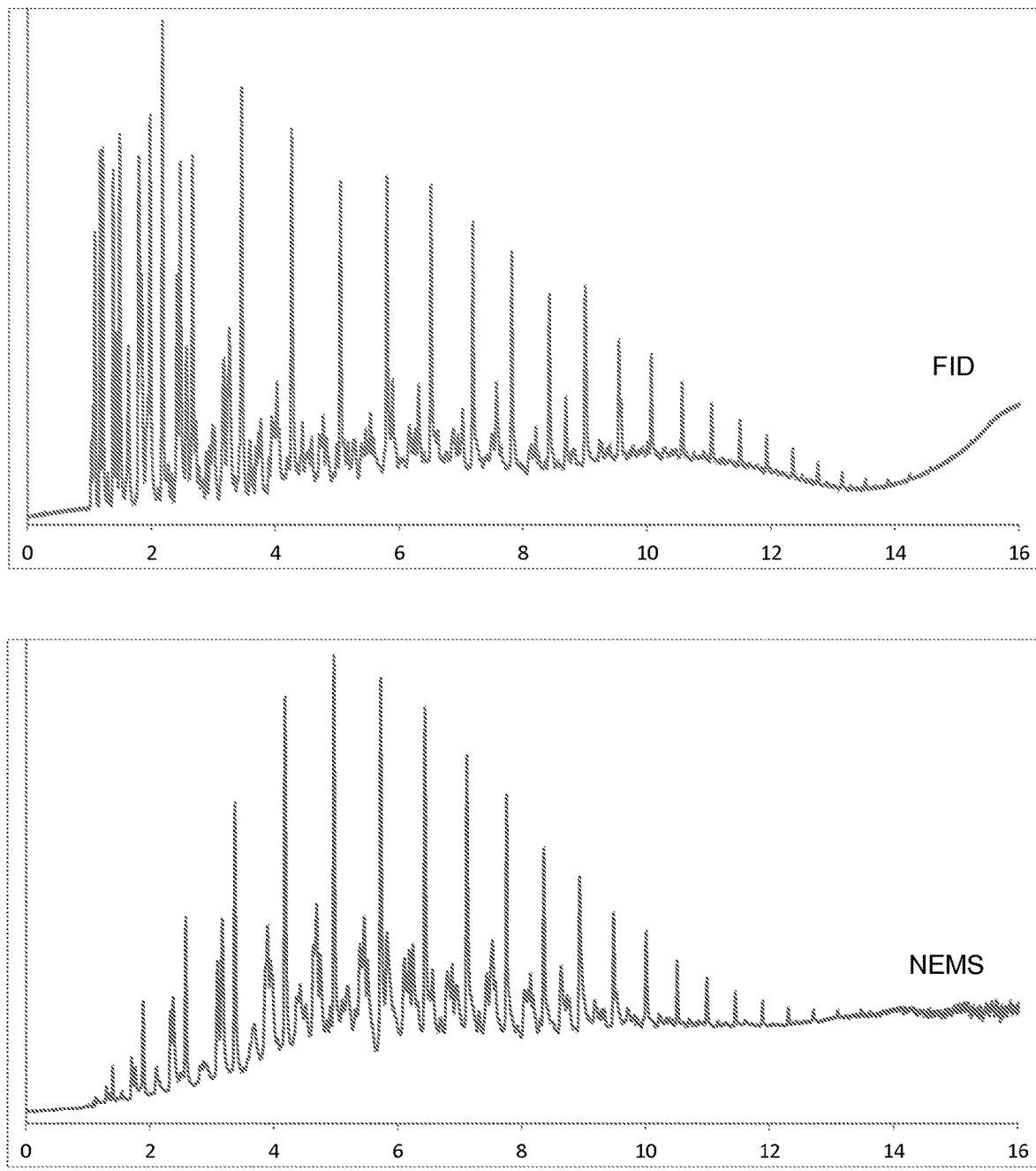
Figure 15:
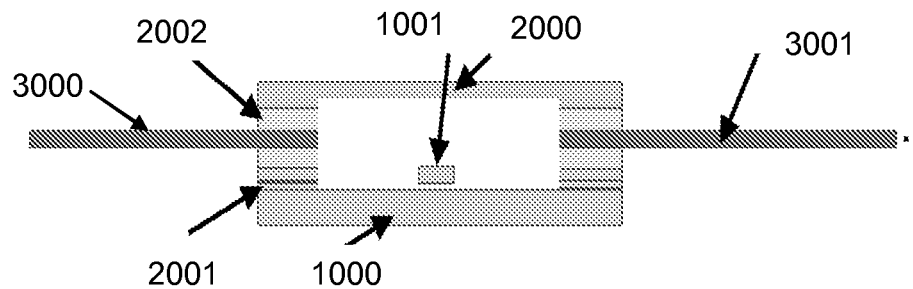
Figure 9:
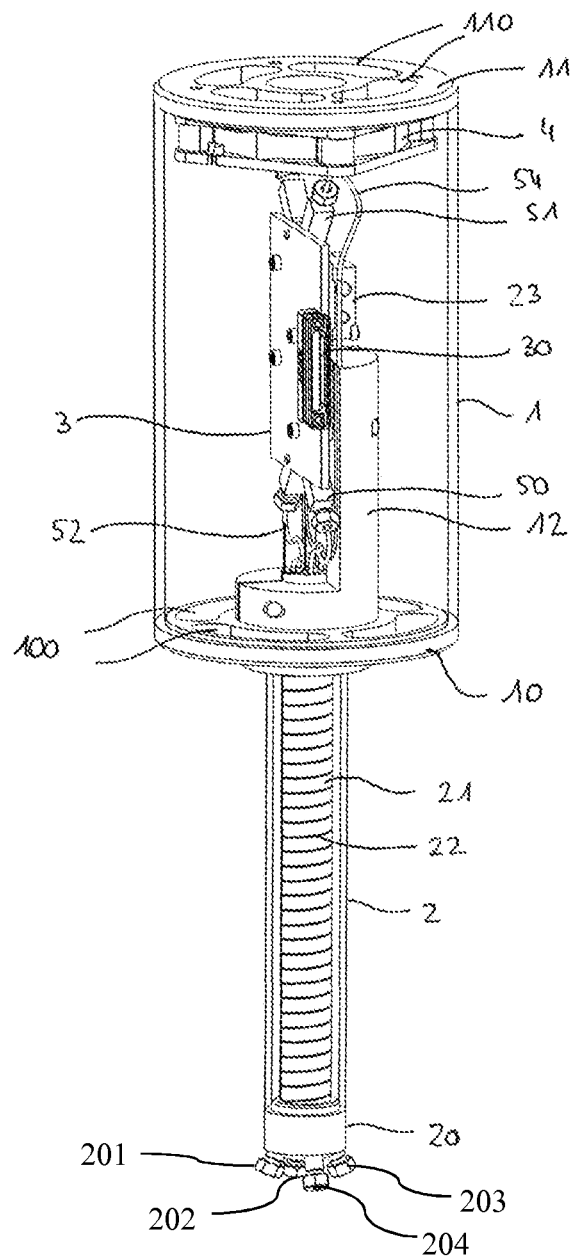
Figure 10:
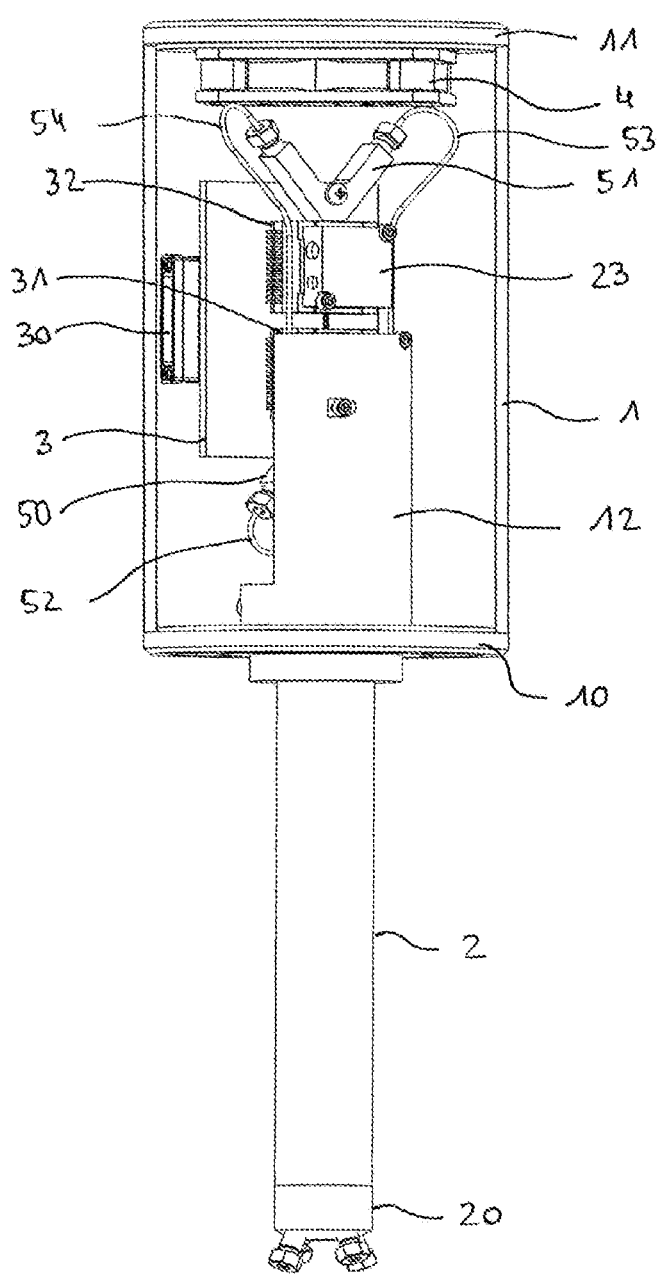
Figure 11:
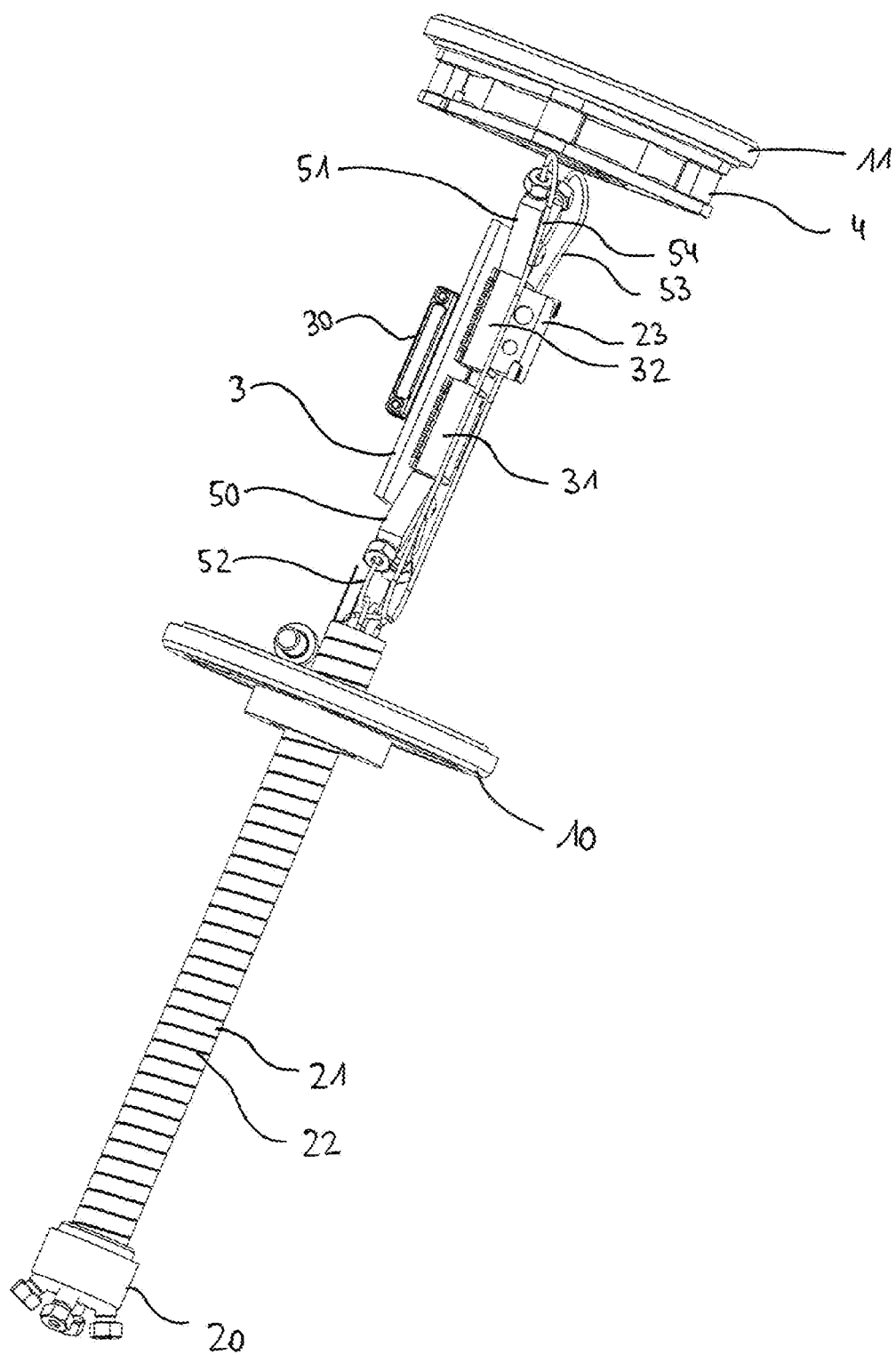
Figure 12:
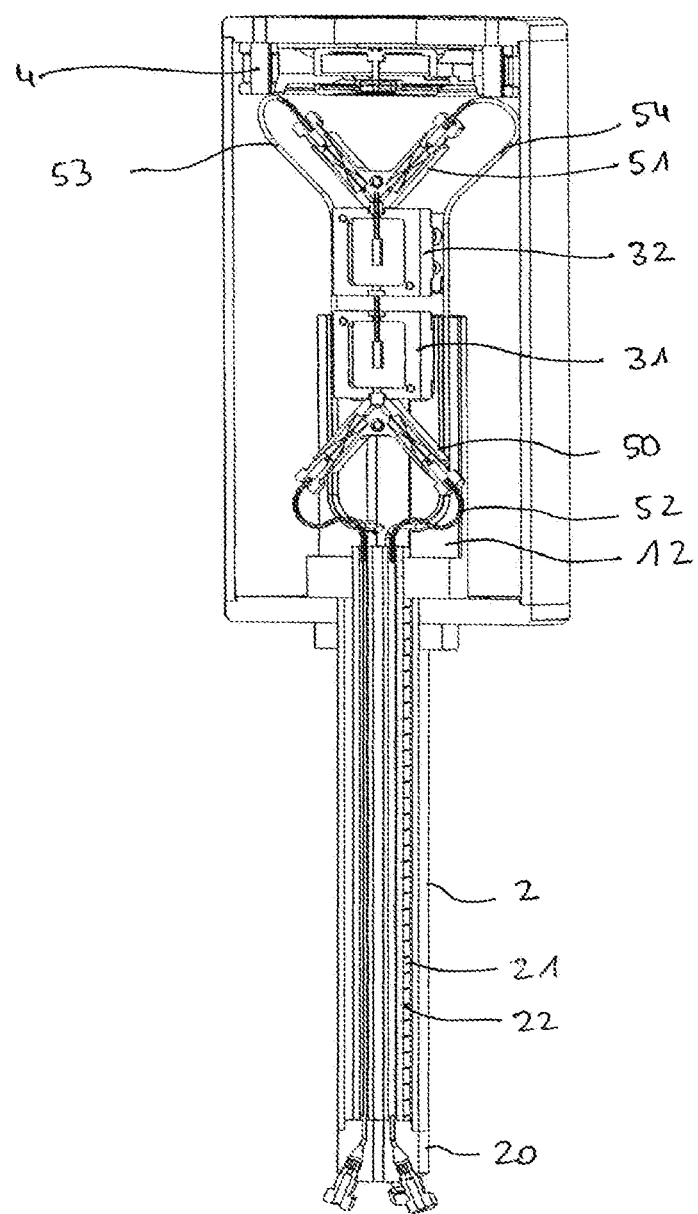
Figure 13:
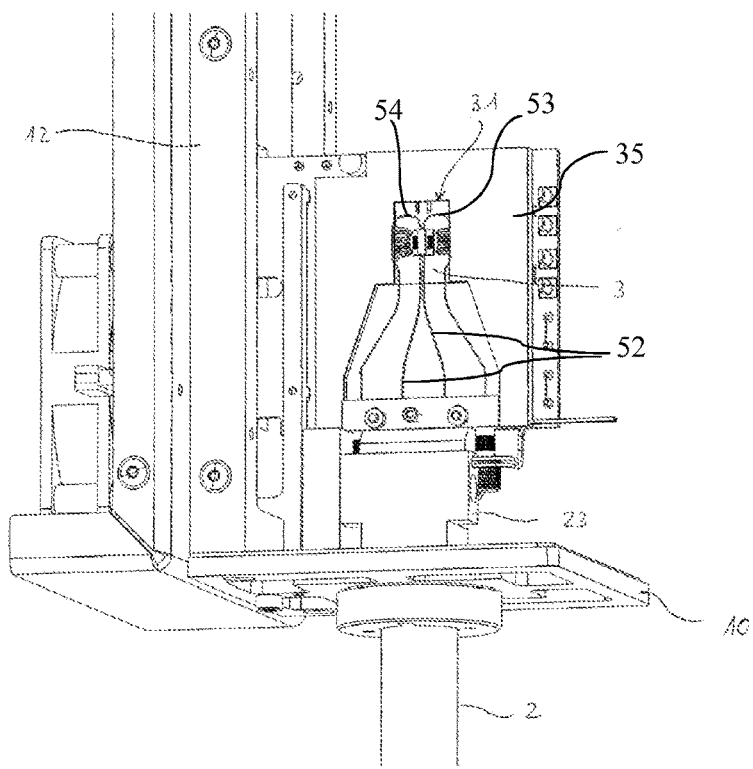
Figure 14:
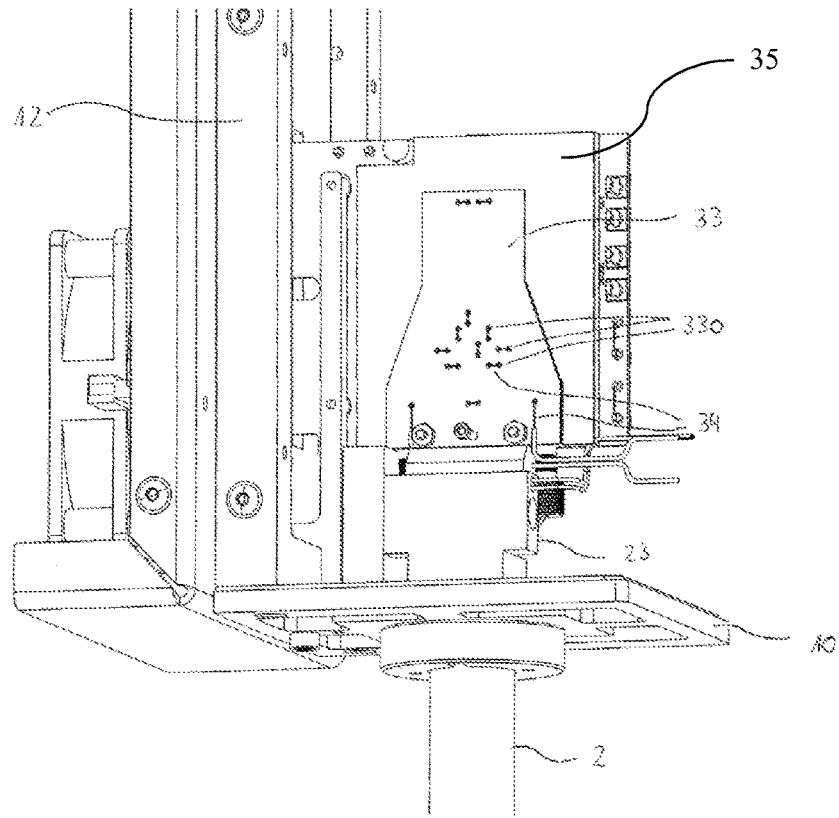

the FIG. 5 shows three chromatograms obtained for a mixture of petrol and C28H58 with a chromatography column encapsulated in a chamber distinct from that of the NEMS resonator, for different temperature differences between the column and the resonator, showing the effect of the thermal decoupling between the two chambers;

FIG. 6 shows chromatograms obtained respectively with an FID detector and a NEMS detector for the mixture of petrol and C28H58 used to produce FIG. 5, while applying the most favourable temperature difference between the chromatography column and the NEMS resonator;

FIG. 7 illustrates chromatograms obtained respectively with an FID detector and a NEMS detector for a condensate, the temperature of the NEMS resonator following a linear profile 60° below the temperature profile of the chromatography column;

FIGS. 8-12 are exploded perspective views of a detector according to an embodiment of the invention;

FIGS. 13 and 14 are partial sectional views of a chamber encapsulating a resonator according to an embodiment of the invention;

FIG. 15 is a sectional view of an embodiment of the fluidic conduit in which the resonator is arranged.

DETAILED DESCRIPTION OF EMBODIMENTS OF THE INVENTION

The invention implements a detector based on at least one NEMS resonator. This detector is intended to be arranged at the outlet of a gas chromatography column in order to detect one or more analytes contained in a sample and separated beforehand by the column. The sample may be in the gaseous state at room temperature; alternatively, it may be liquid at room temperature but heated to a temperature above its boiling point in order to be injected into the column in the vapour state, the column and the resonator as well as the fluidic circuit that connects it being furthermore maintained at a temperature above this boiling point in order to avoid any condensation of the sample. The sample is transported in the chromatography column and the detector by a vector gas.

The resonator is in the form of a beam of which at least one main surface is covered with a functional layer which has a chemical affinity with the analytes of interest.

According to the targeted applications, the functional layer may be polar or apolar.

Optionally, the detector may comprise several resonators, comprising the same functional layer or a different functional layer, chosen as a function of the analytes of interest.

The beam is suspended with respect to a substrate. According to an embodiment, one end of the beam is embedded in the substrate and the opposite end is free, but other solutions to suspend the beam may be envisaged, for example an embedding at the two ends of the beam.

For purely indicative purposes, the dimensions of the beam of such a resonator are of the order of several micrometres in length, several hundreds of nanometres in width, and one hundred or so nanometres thickness.

Thus, according to an embodiment given as an example, the beam has a length of 1 to 100 μm, a width of 50 to 500 nm or even of several μm and a thickness of 50 to 500 nm.

The resonator is enslaved to an electronic reading device configured to make the resonator vibrate at the resonance frequency thereof and to measure a variation of said resonance frequency under the effect of the adsorption or the desorption of an analyte by the functional layer.

When an analyte of interest is adsorbed (or desorbed) on the functional layer, the effective mass of the resonator is modified, which causes a variation of the resonance frequency of the resonator. Thus, the measurement of the variation of the resonance frequency by the reading system makes it possible to measure the variations in mass of the resonator and to deduce therefrom the concentration of gas or vapour to analyse. For a given concentration of analyte, the mass of gas adsorbed and consequently the sensitivity of the measurement depends on the equilibrium constant between the vapour phase and the adsorbed phase of the analyte. This equilibrium constant depends on the temperature of the surface and the physical-chemical characteristics of the sensitive surface. The functional layer thus advantageously has a high adsorbed phase/vapour phase equilibrium constant at a given temperature of use.

For a given concentration and a given nature of functional layer, a decrease in the temperature of the detector increases the mass of analyte adsorbed, which increases the signal delivered by the detector. However, if the temperature of the detector is too low, the adsorption reaction is favoured to excess, which can ultimately lead to condensation on the surface of the detector. There thus exists an optimal operating temperature of the detector for a given analyte of interest. This optimal operating temperature increases approximately like the boiling temperature of the analyte.

The manufacture of a NEMS resonator is known per se and thus does not need to be described in detail in the present text. Reference could notably be made to the documents [Mile2010], EP 2 008 965, WO 2012/034990 and WO 2012/034951, which disclose NEMS resonators capable of being implemented in a detector according to the invention.

It will be noted that, instead of a single NEMS resonator, the detector may comprise one or more arrays of NEMS resonators.

The advantages of an array of resonators with respect to an individual resonator are multiple. On the one hand, the array of resonators offers a total surface for the capture of species to analyse which is all the larger the higher the number of beams. This makes it possible to detect more finely species contained at low concentration in the sample to analyse. Furthermore, the use of an array of resonators makes it possible to minimise the impact of the failure of one thereof, which is compensated by the operation of the other resonators of the array, thus improving the robustness of the detector. Finally, for an array of N NEMS resonators, in theory, a gain in detection limit of the order of $\sqrt{N}$ in terms of signal (or of the order of N in terms of power) should be reached.

Reference could be made to the document WO 2014/053575 for the description of an array of NEMS resonators being able to be implemented in a detector according to the present invention.

Furthermore, in the case where several arrays of NEMS resonators are employed within the detector, it is possible to functionalise these arrays with a functional layer that is different from one array to the next.

Although the term "NEMS resonator" in the singular is used in the remainder of the text, it is understood that the description also applies to a plurality of NEMS resonators, arranged or not in array.

Figure 1:
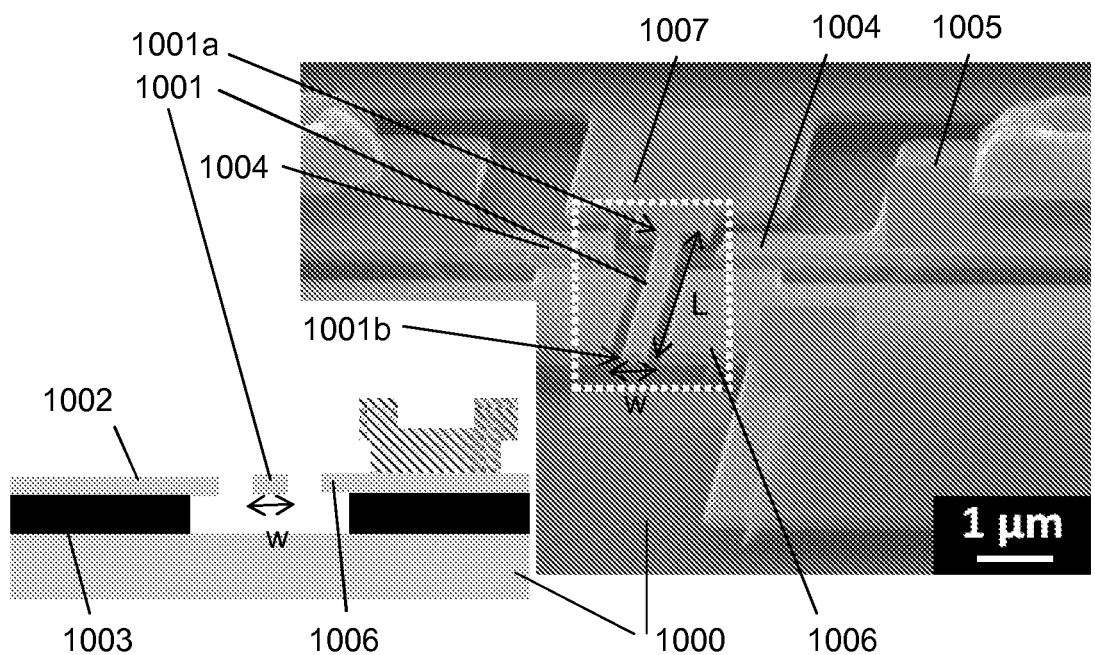
FIG. 1 is a scanning electron microscopy image of a resonator according to an embodiment of the invention, as well as a sectional view of said resonator.

FIG. 1 is a scanning electron microscope view of a NEMS resonator capable of being implemented in a detector according to the invention, as well as a schematic view in transversal section.

Said resonator is advantageously formed on a semiconductor substrate 1000, for example silicon. The substrate 1000 is advantageously covered with an electrically insulating layer 1003 (for example, made of silicon oxide) and a silicon layer 1002, to form a SIO (Silicon On Insulator) type substrate.

The resonator comprises a beam 1001 of length L and of width w.

The beam 1 is suspended with respect to the support substrate 2, with the exception of an embedding of one of its ends 1001a in a part of the substrate 1000, projecting with respect to the plane of the substrate which extends under the beam.

The other end 1001b of the beam is for its part free.

In a manner known per se, such a beam may be formed in the layer 1002, by means of an etching making it possible to delimit the beam and to eliminate the part of the electrically insulating layer 1003 situated under the beam 1001, in order to free it.

On either side of the beam extend two strain gauges 1004, for example piezoresistive, which are also suspended with respect to the substrate 1000.

Advantageously, said gauges are, like the beam, etched in the SOI substrate and have at least one plane in common with the beam.

These gauges are advantageously made of doped semiconductor material, preferably having a concentration of dopants greater than $10^{19}$ atoms/cm$^3$.

Preferably, said doped semiconductor material is doped silicon.

The intersection between each of the gauges and the beam lies at a distance from the embedding region of the beam, chosen to maximise the strain exerted on the gauge during deflection of the beam.

Each of the gauges 1004 is connected to an electrode 1005, said electrodes enabling the application respectively of constant potentials of opposite signs.

In other embodiments of the resonator, it is possible to only employ one strain gauge made of doped semiconductor material.

The resonator further comprises a device for electrostatically actuating the beam 1001 which, as represented here, may comprise two electrodes 1006 extending in the same plane as the beam and arranged on either side thereof, at a determined distance.

The electrodes 1006 are intended to receive respectively an electrical excitation signal and a signal of opposite sign, and thus constitute two inputs of the resonator.

Under the application of an electrical signal having a frequency corresponding to the empty resonance frequency of the beam, the beam is made to vibrate in a plane parallel to the substrate.

Empty resonance frequency of the beam is taken to mean the resonance frequency of the beam in the absence of the sample to analyse.

According to an embodiment, the measurement of the variation of electrical resistance of the piezoresistive gauges is carried out between the embedded end of the beam and the junction between the beam and the gauges.

The output signal of the resonator is thus supplied to a connection electrode 1007 situated at the level of the embedded end of the beam, with a view to the reading of said signal.

This measurement method is not however exclusive and the output signal may be provided by other means; for example, it is possible to apply a polarisation voltage at the level of the electrode and to measure the voltage at the terminals of the assembly of the two gauges to deduce therefrom the variation of their electrical resistance.

Those skilled in the art will thus be able to adjust the design of the polarisation of the strain gauge(s) and the measurement of their response without however going beyond the scope of the present invention. Furthermore, another actuation mode could be used without going beyond the scope of the invention.

In a particularly advantageous manner, the NEMS resonator may be formed on a chip of several millimetres sides, said chip being able to be embedded on a printed circuit as will be described in detail below.

To make it possible to control the temperature of the NEMS resonator, said resonator is encapsulated in a regulated temperature chamber.

The volume of the chamber is chosen to be just sufficient to encompass the resonator and the chip on which it is formed, while minimising free spaces in order to optimise the energy consumption required to regulate the temperature in the chamber.

The chip on which the NEMS is formed being of small dimensions, the inner volume of the chamber may be particularly small (of the order of several mm$^3$ or tens of mm$^3$). This has several advantages. On the one hand, the electrical power to implement in order to regulate the temperature within the chamber is reduced. On the other hand, for a given power, the speed of heating and cooling is increased with respect to a chamber of larger volume. Finally, the thermal decoupling of the chamber of the detector vis-à-vis the chromatography column is also easier.

The control of the temperature in the chamber is ensured by a temperature regulating unit.

Said regulating unit may comprise heating means and/or cooling means, as well as a temperature sensor and a feedback loop making it possible to apply inside the chamber a temperature conforming to a determined profile. Said temperature profile may be defined by a user as a function of the composition of the sample to analyse and the searched for analytes.

The feedback loop typically comprises a calculator communicating with a user interface and configured to receive the temperature profile to apply and measurement data of the temperature sensor, and, from these input elements, to command the heating and/or cooling means to reach the desired temperature within the chamber over time.

The temperature sensor may be a platinum resistance thermometer widely used in electronic devices, notably of the Pt100 type.

In a particularly advantageous manner, the regulating unit comprises a heating element arranged inside the chamber. For reasons of compactness, said heating element may be a heating resistance supplied by an electric current.

Preferably, the regulating unit further comprises a cooling system. Different cooling technologies may be envisaged: fan, Peltier cell, fluidic cooling circuit, potentially combined. Those skilled in the art are able to choose and to dimension the cooling system as a function of the arrangement of the chamber and the expected performances. The cooling system makes it possible in particular to cool rapidly the inner volume of the chamber after a detection phase at high temperature, and thus allows the rapid implementation of a new detection phase at lower temperature.

The chamber is not necessarily hermetically sealed nor thermally insulated from the exterior. Conversely, it may comprise vents which enable faster evacuation of heat when it is wished to cool the resonator. Furthermore, the inner volume of the chamber may be at least in part heated by passive thermal transfer from outside the chamber (for example due to its proximity vis-à-vis the chromatography column which is itself heated).

Apart from the effective mass of the resonator, the resonance frequency of the NEMS resonator also depends on the temperature of the detector, the flow rate of the vector gas and other exogenous factors.

Hence, the base line of the measurement signal varies with temperature. There is thus a superposition between the signal useful for the measurement (i.e. the variations of resonance frequency of the NEMS resonator linked to adsorption/desorption of gas) and a non-useful background signal (temperature variation of the NEMS resonator, and other exogenous factors making the resonance frequency of the resonator vary).

Figure 2:
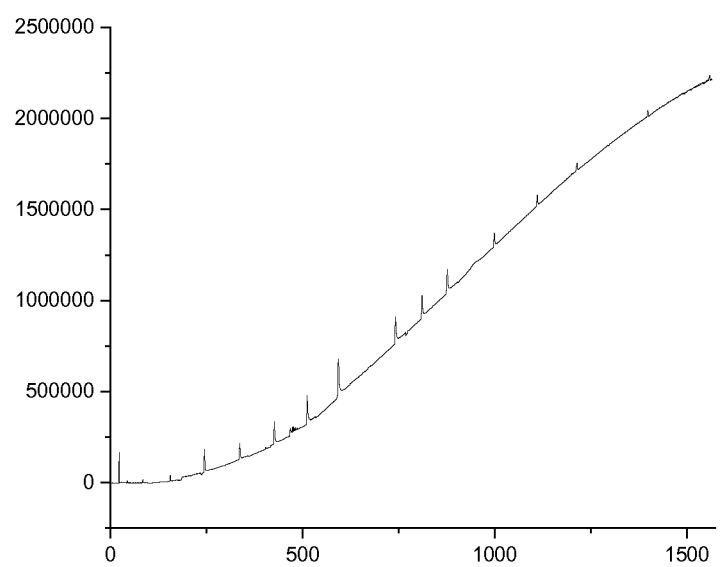
FIG. 2 is a raw chromatogram (response of the detector as a function of time (in seconds)) obtained with a detector according to an embodiment.

As an example, FIG. 2 shows a raw chromatogram obtained with a NEMS resonator of which the working temperature varies according to a linear temperature profile varying between 40 and 250° C. at a rate of 20° C. per minute. The variation of frequency and the small signal to background noise ratio linked to the temperature ramp applied to the NEMS, which penalises the identification of the different peaks, may be clearly observed.

Advantageously, a so-called differential reading of the NEMS resonator is thus implemented which makes it possible to reduce these independent variations of the variation of mass created by adsorption of an analyte of interest and to highlight uniquely the variations of the resonance frequency of the NEMS resonator by adsorption/desorption of gas.

Figure 3:
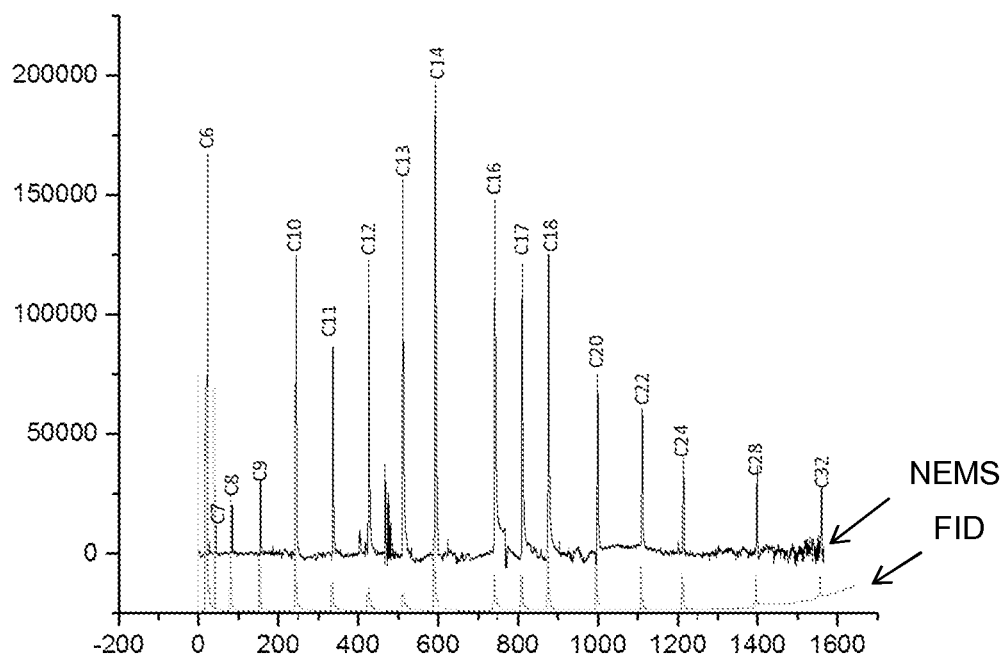
FIG. 3 is a chromatogram (response of the detector as a function of time (in seconds)) obtained after subtraction from the chromatogram of FIG. 2 the base line of the blank response of said detector.

To this end, a first approach consists in carrying out a so-called blank analysis for which no sample is injected into the chromatography column while applying the temperature profiles on the column and the NEMS detector necessary for the analysis. For this analysis, it is possible to inject into the system uniquely the vector gas, or to work with an empty gas circuit. In this way, it is possible to collect the variations of the base line of the detector linked to any other phenomenon than the adsorption and the desorption of gas. Next, an analysis is carried out by injecting the sample and by applying the same temperature profiles as during the blank analysis. Finally, in a so-called offline processing, the blank measured base line is subtracted from the base line measured with the injection of the sample in such a way as to only conserve the variations in base lines of the detector linked to the adsorption/desorption of the different gas peaks. FIG. 3 (NEMS curve) illustrates the result of such a processing carried out on the chromatogram of FIG. 2. As a comparison, the response of an FID detector is displayed on the chromatogram (FID curve), which makes it possible to verify the correct correspondence of the peaks detected with the two techniques.

The chromatograms of FIGS. 2 and 3 were obtained for a simple mixture of hydrocarbons. FIG. 3 shows that compounds with up to 32 carbon atoms were able to be detected by the NEMS resonator, which confirms the capacity of the NEMS resonator to analyse hydrocarbons.

Figure 4:
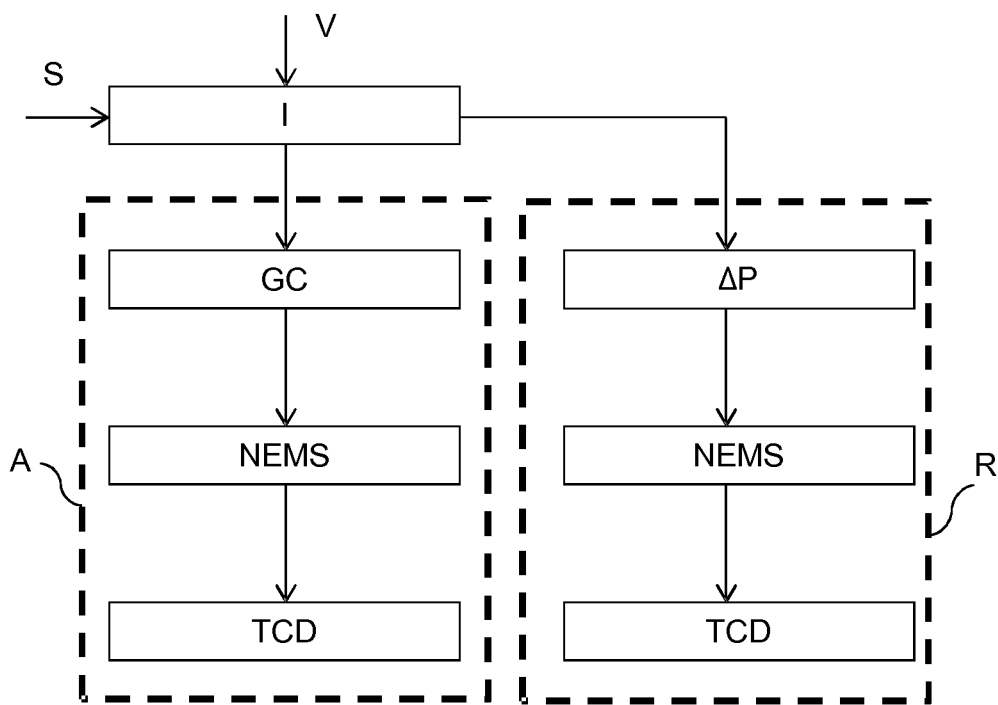
FIG. 4 is a block diagram of a differential reading device making it possible to be free of base line variations linked to exogenous phenomena.

Another differential reading approach consists in measuring simultaneously in the course of the same analysis phase the variation of resonance frequency of two resonators differentially (or, if a TCD detector is associated with the NEMS detector, two couples each formed of a NEMS resonator and a TCD detector). As illustrated in FIG. 4, one of these couples is arranged on the analysis pathway A and thus measures the different peaks of analytes and any other exogenous phenomena. The other couple is arranged on a so-called reference pathway R and thus only measures exogenous phenomena. The system comprises, upstream of the two pathways, an injector I which receives a part of the sample S in gaseous and vapour form and the vector gas V and which mixes it before injecting it, on the one hand into the chromatography column noted GC, which is on the analysis pathway A, and on the other hand into a conduit AP having a head loss identical to that of the column, on the reference pathway R. Through an electronic that differentiates the measurement signals derived from two couples of detectors, only the signals derived from the adsorption/desorption of the different gas peaks are thus conserved. This approach is preferred in so far as it does not require blank analysis nor offline processing.

NEMS resonators are capable of having non-negligible interactions (called fluidic interactions) with a surrounding gas.

Consequently, apart from the variation of resonance frequency of the resonator, it is possible to measure the variation of resonance amplitude due to the fluidic interactions between the resonator and the sample.

As described in the document EP 2 878 942, it is possible to deduce from this variation of amplitude a fluidic characteristic of the sample. This fluidic characteristic is advantageously a viscosity, an effective viscosity, an average free course of the molecules, a flow rate and/or a thermal conductivity of the sample. "Effective viscosity" is taken to mean in the present text a viscosity parameter taking account of the regime of rarefaction of gases in the Reynolds equation simplifying the Navier-Stokes equation (cf. paragraph 5.1 of [Bao2007]).

It has furthermore been demonstrated that the contrast between the fluidic characteristics of the vector gas and those of the sample to analyse is all the greater when the temperature to which the NEMS resonator is subjected is high. In the system described in the document EP 2 878 942, the NEMS resonator is heated by Joule effect in order to minimise the influence of adsorption phenomena with respect to fluidic interactions.

On the other hand, the fact of heating the NEMS resonator makes it possible to decrease the effective viscosity of the sample and the vector gas and thus to increase the variation of amplitude measured by the reading device.

The present invention may thus benefit from the fact that the resonator is heated in the chamber to implement, with good sensitivity, a measurement of at least one fluidic characteristic according to the principle described in the document EP 2 878 942, while being free of the Joule effect heating system used in this system.

The combination of the measurement of frequency variation and the measurement of amplitude variation makes it possible to obtain more information on the sample, which makes it possible to differentiate more precisely analytes have a similar response.

On account of the low level of response of the NEMS resonator to light compounds (C1-C6), it may be desirable, according to the application needs, to couple it in series to a micro-catharometer (also called TCD detector in the remainder of the text), which is more sensitive to these species. The two detectors being non-destructive, the TCD detector may be arranged in the same fluidic conduit as the NEMS resonator, upstream or downstream thereof.

The TCD detector may be placed in the same chamber as the NEMS detector, in order to facilitate the integration of said detectors, for example on a same chip or a same printed circuit. Alternatively, the TCD detector may also be implemented outside the chamber of the NEMS detector, its sensitivity not being directly influenced by its working temperature.

The TCD detector is known per se and will thus not be described in greater detail in the present text.

The detector that has been described is particularly suited to implementation in a gas analysis system comprising a gas chromatography column and a detector arranged at the outlet of said column.

The chromatography column is arranged in a temperature regulated chamber and thermally decoupled from the chamber in which the resonator is encapsulated. Upstream of the chromatography column, an injector makes it possible to vaporise the sample and to mix it with the vector gas. For hydrocarbons, a split injection is generally implemented, that is to say that only a fraction of the vaporised sample driven along by the vector gas is injected into the column.

A fluidic conduit (for example in the form of a capillary tube) connects the outlet of the chromatography column to the inlet of the detector.

To maximise the thermal decoupling between the two chambers, it is preferable to increase the distance between the chambers and to heat the connecting conduit to avoid any cold point in which condensation could occur.

Thanks to this thermal decoupling, it is possible to adjust the temperature profiles in each of the two chambers independently, which makes it possible to manage the temperature of the NEMS resonator whatever the temperature of the chromatography column.

Unlike other detectors employed in chromatography, a NEMS resonator has an optimal detection temperature which depends on the analyte of interest.

If the resonator is at a too high temperature, the adsorption of gas is less efficient and consequently the measurement sensitivity is lower. Furthermore, a too low temperature of the resonator may cause deformation of the peaks (which are, for a well dimensioned analytical system, of gaussian shape) at the outlet of the column (resulting in a greater peak trailing edge), decreasing the separating power of the chromatography column, and/or fouling the functional layer (the adsorption sites not being freed), decreasing the efficiency thereof over time.

To optimise the performances of the NEMS resonator, it is necessary to finely control the working temperature thereof to maintain it close to this optimal value for each analyte of interest. It is thus useful to dynamically adapt the temperature of the resonator as a function of the analytes which come out of the column, in the same way as the chromatography column is temperature regulated to control the speed of analysis and separation. To cover a wide range of gaseous compounds to detect, it is desirable to control the resonator over a temperature range as wide as possible, typically between room temperature (20° C.) and 350° C.

For numerous applications of analysis of complex mixtures, it is often appropriate to conduct a temperature rise profile, for example in the form of a linear ramp, on the chromatography column to separate the gaseous compounds retained by the column. The working temperature of the NEMS resonator does not necessarily have to be identical to that of the column to optimise the detection performances thereof. In most cases, it is moreover preferable that the temperature of the NEMS resonator is below that of the column, which enables thermal decoupling between the two chambers.

According to an embodiment, the regulation of the temperature of the NEMS resonator may be based on the temperature in the chamber of the chromatography column. For this purpose, the heating element of the chamber containing the chromatography column comprises a temperature sensor (of Pt100 or thermocouple type), in order to measure the temperature of the chromatography column at any time. The temperature of the chamber containing the NEMS resonator may be adjusted in real time as a function of the temperature in the chamber containing the chromatography column. In other words, the temperature T_NEMS of the NEMS resonator is adapted according to a law T_NEMS=f (T_GC) where f is a programmable analytical function and T_GC the temperature in the chamber of the chromatography column, measured by the aforementioned temperature sensor.

An example of temperature profile of the NEMS resonator consists for example in applying a constant temperature difference between the temperature of the column and that of the NEMS resonator. The temperature regulation law is then T_NEMS=T_GC−ΔT, where ΔT is a constant.

FIG. 5 shows three chromatograms obtained with a chromatography column encapsulated in a chamber distinct from that of the resonator, showing the effect of thermal decoupling between the two chambers.

The sample to analyse is a solution of relatively light petrol comprising a concentration of C28H58, which is a relatively heavy hydrocarbon, of 5000 mg/L.

The temperature profile in the chamber of the chromatography column is identical in the three cases: it involves a linear temperature rise ramp of 20° C. per minute, between 50° C. and 300° C. (noted GC on the temperature profiles shown on the right of the curves).

Chromatogram A was produced by applying in the chamber of the resonator a temperature rise ramp (noted NEMS) identical to that of the column (noted GC) (difference between the two ramps =0° C.).

Chromatogram B was produced by applying in the chamber of the resonator a temperature ramp of 20° C. per minute, but triggered with a delay of one minute, such that the difference between the two temperature ramps is 20° C.

Chromatogram C was produced by applying in the chamber of the resonator a temperature ramp of 20° C. per minute, but triggered with a delay of three minutes, such that the difference between the two temperature ramps is 60° C.

Comparison of chromatograms A, B and C shows that the highest temperature difference between the temperature profile of the column and that of the resonator procures the best sensitivity to the C28H58 peak.

It will however be noted that a too high temperature difference no longer procures such an improvement.

Consequently, for the detection of hydrocarbons having long carbon chains, preferably a temperature difference is chosen between the chamber of the resonator and the chamber of the chromatography column comprised between −5 and −150° C., preferably between −30 and −100° C., or even between −30 and −70° C., and in an even more preferred manner between −40 and −60° C., for example equal to −50° C.

Naturally, other strategies of temperature profile of the NEMS resonator may be adopted according to the targeted applications. In particular, the temperature difference between the chromatography column and the NEMS resonator is not necessarily constant over time.

The chromatograms of FIG. 6 were obtained for the same mixture of petrol and C28H58, respectively with an FID detector (upper curve) and a NEMS resonator according to the invention, while respecting a temperature difference of −60° C. between the chromatography column and the resonator. These two curves do not have the same scale along the Y-axis, but make it possible to verify that the C28H58 peak is indeed detected with the NEMS resonator.

The chromatograms of FIG. 7 were for their part obtained from a condensate which is a real petroleum fraction. The upper curve represents the signal of the FID detector, curve B represents the signal of the NEMS detector, the difference in temperature between the chromatography column and the NEMS resonator being −60° C.

Although the condensate constitutes a much more complex mixture than in the preceding case, a good correlation is observed between the FID signal and the NEMS signal, and notably clearly marked peaks of the NEMS signal.

To avoid saturation of the NEMS resonator, it could be necessary to make sure not to inject a too large sample into the chromatography column. Those skilled in the art will thus be able to adjust the split ratio between the volume of sample actually injected into the chromatography column and the total volume of the vaporised sample.

It will be noted that the fact of heating the NEMS resonator, and in particular in a dynamic manner according to a temperature profile, goes against normal practice in the gas analysis field. Indeed, involving a gravimetric detection of which the sensitivity is directly linked to an adsorption mechanism, which is penalised by heat, it is contrary to custom to maintain the NEMS resonator at a relatively low and stable temperature. Furthermore, the polymer functional layer normally used to functionalise the NEMS resonator is not suited to operating at such high temperatures as those provided in the present invention.

Thus, the system according to the invention procures a particularly relevant alternative to FID detectors for the analysis of hydrocarbons, notably heavy hydrocarbons. Indeed, the NEMS detector has performances at least equal to that of an FID detector while being free of the defects thereof (destructive character, limitation to carbon chains, presence of hydrogen and a flame), which enables use in constrained environments.

Application 1: Molecular Description of Hydrocarbons and Assay

According to an embodiment, the functional layer covering the NEMS resonator is an apolar phase. Such a resonator arranged at the outlet of a gas chromatography column makes it possible to describe at the molecular scale, and in a repeatable manner, the composition of petroleum fluids in the gaseous or liquid state, from a qualitative and quantitative viewpoint.

According to another embodiment, the functional layer covering the NEMS resonator is a polar phase. Such a resonator arranged at the outlet of a gas chromatography column makes it possible to describe at the molecular scale, and in a repeatable manner, the composition of sulphur, oxygen or nitrogen containing molecules of petroleum or refined fluids in the gaseous or liquid state, from a qualitative and quantitative viewpoint.

In both cases, the molecular analysis that is carried out thanks to the system according to the invention enables a large number of applications in the oil sector.

A first application is the analysis of the compartmentalisation and connectivity of reservoirs. Thus, the molecular analysis makes it possible to determine the similarities and the differences in the composition of hydrocarbons of 1 to 50 carbon atoms by statistical approaches in order to determine the zones that may be produced by a well and to better understand the flows of fluids in oil reservoirs.

Another application relates to the allocation of production. From the molecular analysis, it is in fact possible to calculate by statistical approaches the proportions of fluids originating from different reservoirs which contribute to the mixed production: from a same well, from different wells, from different platforms and from different fields.

Another application relates to the evaluation of the integrity of wells. From the molecular analysis, it is possible to identify by statistical approaches the origin of fluids that could belong in an oil well annulus by comparing the composition of the products found in an annulus with those of the fluids of all the reservoirs crossed and/or intra-annulus process.

Another application relates to the prediction and the description of the composition of fluids in a reservoir formation. The description of the molecular compositions of the fluids obtained thanks to the gas analysis system may be used in the determination of the properties of the fluids (in particular their phase state in reservoir conditions, their density, their viscosity, etc.) via thermodynamic models.

Another application relates to the description of the fluid composition at a given depth within a formation by a direct measurement in the depth conditions. This composition may next be compared constituent by constituent with that of another depth to determine the evolution thereof.

Finally, in the case where the functional layer is a polar phase, the molecular analysis makes it possible to ensure a monitoring of sulphur containing fractions in the loads of hydrodesulphurisation units in refineries.

The different techniques for exploiting the molecular analysis provided by the gas analysis system are known per se and will thus not be described as such in the present text.

Application 2: Molecular Description of Hydrocarbons and Assay in Water

According to an embodiment, the functional layer covering the NEMS resonator is an apolar phase. Such a resonator arranged at the outlet of a gas chromatography column coupled to an extraction/pre-concentration system makes it possible to describe on the molecular scale, and in a repeatable manner, the composition of any type of hydrocarbon in water.

According to another embodiment, the functional layer covering the NEMS resonator is a polar phase. Such a resonator arranged at the outlet of a gas chromatography column coupled to an extraction/pre-concentration system makes it possible to describe on the molecular scale, and in a repeatable manner, the composition of any type of sulphur, oxygen or nitrogen containing hydrocarbon in water.

In both cases, the molecular analysis which is carried out thanks to the system according to the invention enables a large number of applications in environmental analyses in the oil sector.

A first application relates to the assay of polycyclic aromatic hydrocarbons (PAH), polychlorobiphenyls (PCB), BTEX (benzene, toluene, ethylbenzene, xylene), alkanes, alkenes and/or other environmental target molecules in synthetic or real water (sea, discharges, rivers, reservoirs, etc.) after liquid-liquid extraction (organic solvent non-miscible with water).

Another application relates to the assay of HAP, PCB, BTEX, alkanes, alkenes and/or other environmental target molecules in synthetic or real water after extraction of the headspace (so-called "headspace" analysis).

Another application relates to the assay of HAP, PCB, BTEX, alkanes, alkenes and/or other environmental target molecules in synthetic or real water after extraction in solid phase of type SPE (solid phase extraction), SPME (solid phase microextraction), SBSE (stir bar sorptive extraction), or on any other solid or membrane material capable of creating favourable sharing coefficients with water.

Another application relates to the tracing of natural or industrial leakages of hydrocarbons in the natural environment, not only for exploration needs but also for the control of base installations (pipes, valves, risers, etc.) and the monitoring of the quality of water. The molecular analysis of hydrocarbons in water may in fact provide crucial information such as the early detection of leakages, the identification of the leakage source, etc.

Application 3: Tracking of Tracers

Whether the functional layer covering the NEMS resonator is an apolar phase or a polar phase, the resonator arranged at the outlet of a gas chromatography column makes it possible to detect any type of natural or synthetic tracer in petroleum fluids and consequently to track said tracer selectively.

A particularly advantageous application of the invention is then the qualitative and quantitative analysis of artificial tracers (injected or integrated in the completions) for the purposes of allocation of production and determining the origin of fluids.

Figure 8:
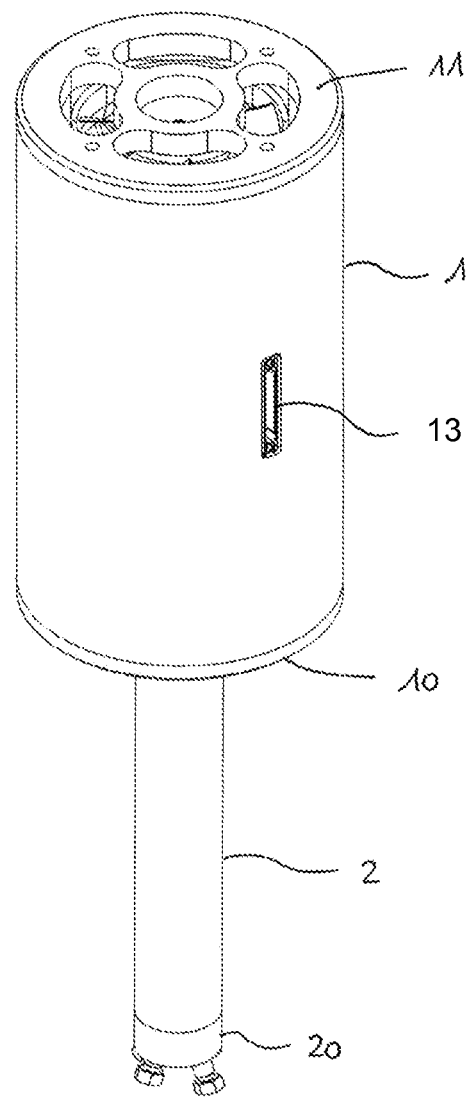

FIGS. 8 to 12 illustrate an exemplary embodiment of a detector comprising a first regulated temperature chamber in which a NEMS detector and a TCD detector are embedded. FIG. 8 is a perspective view of the detector arranged in said first chamber; FIGS. 9 to 12 are partial sectional views according to different angles.

The TCD and NEMS detectors are mounted in series on a printed circuit board 3. The detectors are arranged in the form of modules 31, 32 electrically connected to the printed circuit 3. For example, the module 31 comprises one or more NEMS detectors and the module 32 comprises one or more TCD detectors. Each module may comprise two detectors of the same type, one serving as reference and the other being used for the analysis with a view to the differential measurement mentioned above.

According to another embodiment (not illustrated), a first module comprises an array of NEMS resonators with a polar functional layer and a second module comprises an array of resonators with a different functional layer, for example apolar. Any other configuration of the modules may naturally be envisaged.

In a particularly advantageous manner, each module forms a second regulated temperature chamber in which the resonator or array of resonators is encapsulated.

The first chamber is formed by assembly of a cylindrical shell 1 and two flanges 10, 11 arranged at the ends of the shell. The shell 1 has an opening 13 for the passage of a connector 30 mounted on the printed circuit 3 and serving to connect electrically the detectors to an external processing system. The flanges 10, 11 have openings (vents) 100, 110 enabling faster evacuation of heat. Naturally, any other structure could be chosen for the chamber without however going beyond the scope of the present invention.

A fan 4 is arranged at one end of the chamber, the rotational plane of the blades being perpendicular to the longitudinal axis of the shell 1.

At the end opposite to the fan is arranged a mandrel 21 around which is arranged the heating element 22 which is in the form of a heating filament wound around the mandrel. The mandrel 21 and the heating element 22 are arranged in a tube 2.

Inside the mandrel 21 pass capillary conduits suited to being fluidically connected to the chromatography column via a connector 20. This connector comprises two inlets 201, 202 and two outlets 203, 204. The two inlets supply the two detectors (measurement and reference). The two outlets coming from the two detectors make it possible to connect in series and downstream thereof other detectors or a vent. Thus, the capillary conduits do not have any cold point liable to cause condensation of the sample.

Inside the first chamber is arranged a support 12 intended to support the printed circuit 3 as well as the capillary conduits 52, 53, 54 which ensure a fluidic connection between the column and the detectors. The conduit 52 makes it possible to introduce the sample into the module 31 via the inlet device 51; the conduits 53 and 54 are arranged symmetrically on either side of the modules 31, 32. They make it possible to transfer the sample from the NEMS detector to the connector 20.

The support 12 also supports a heating unit 23 comprising a heating cartridge and a temperature probe making it possible to monitor in real time the temperature in the first chamber.

FIGS. 13 and 14 show two partial sectional views of a module 31 containing a NEMS detector. The arrangement of the components in the first chamber is slightly different to that of FIGS. 8-12, but the module of FIGS. 13-14 may be used in this embodiment with some adaptations within the reach of those skilled in the art. With respect to the embodiment of FIGS. 8-12, the heating unit 23 is arranged in the first chamber on the flange 10, facing the tube 2 containing the mandrel and the heating wire wound thereon. The capillary conduits arranged in the mandrel pass through the unit 23 in which they are heated to a suitable temperature, in order to open out in the actual module.

The module 31 comprises a stack of electrically and thermally insulating plates, for example made of mica, which form a second chamber around the NEMS resonator and the capillary conduits which are in fluidic connection therewith. The resonator is arranged on a chip electrically connected to the printed circuit 3, at the centre of the rectangle designated by the reference 31. Only a part of said printed circuit is visible in FIG. 13, the remainder being masked by an insulating plate 35 which defines an inner volume in which the resonator and the capillary conduits are arranged. This volume is closed by a plate 33 visible in FIG. 14. Said plate 33 is provided with a plurality of holes 330 through which a heating wire 34 having a high electrical resistivity is passed. The holes 330 are arranged on the surface of the plate 33 such that the route of the heating wire enables uniform heating of the capillary conduits and the NEMS resonator. Although not visible in FIGS. 13 and 14, a temperature sensor is arranged in the module 31 in order to measure in real time the temperature inside said module. Said temperature is enslaved to a determined temperature profile by means of a feedback loop which comprises a calculator (not represented) connected on the one hand to the temperature sensor, from which it receives the measurement data, and to an electrical source connected to the heating wire, to which it sends intensity set values of the electric current to pass in the heating wire to reach the desired temperature. Advantageously, the calculator is embedded on the printed circuit 3, such that the detector is entirely autonomous. The inner volume of the second chamber being extremely small, the temperature may be controlled therein in real time in a very fine manner over a wide temperature range.

Naturally, these particular arrangements of the detector are given uniquely as non-limiting examples. In particular, the heating element may be in a form other than a resistive wire, for example in the form of a bar or a flat plate, which makes it possible to simplify its assembly on a wall of the second chamber, notably with a view to production on an industrial scale. Any other heating element suited to the dimensions of the second chamber may be used.

In order to cover a wide working temperature range of the detector, the materials that constitute it are chosen to withstand a temperature of the order of 300° C.

The shell and the flanges which define the envelope of the first chamber are typically made of metal.

With regard to the printed circuit board that supports the resonator, the favoured material is a ceramic or polyimide (Kapton™) for example.

The NEMS resonator and, if appropriate, the TCD detector, are advantageously made of doped silicon or silicon nitride ensuring mechanical rigidity and electrical conduction. Doped silicon is indeed capable of withstanding temperatures of more than 400° C. without modification of the electronic and mechanical properties thereof. The TCD detector is coated with a platinum layer conserving all of the physical properties thereof well above 300° C.

As regards the functional layer, the polymers that are conventionally used to functionalise NEMS resonators are generally not useable in the present invention, because they withstand heat poorly. Indeed, the deposition temperature of these polymers is of the order of 100° C. to 200° C. depending on their nature. Consequently, in the present invention, the NEMS resonator is advantageously functionalised with a porous oxide layer derived from micro-electronics deposited at high temperature (of the order of 400 to 500° C.) which offers good chemical responses over a wide range of molecules (alkane, alkene, alcohol, aromatic compounds, etc.). Advantageously, the composition of said oxide is of generic formula $SiO_xC_yH_z$ (with x>0 and y and z≥0), for example SiOC, $SiO_2$, SiOH, etc. Such a porous oxide is notably described in the document WO 2015/097282. An aluminium oxide, of generic formula AlxOy (with x and y>0), for example $Al_2O_3$, could also be used.

To produce the fluidic flow line encompassing the NEMS resonator and the TCD detector, on the substrate 1000 that supports them is assembled a structured lid 2000 made of glass or silicon with glass frit 2001 of which the process of heat soldering is carried out around 400° C. FIG. 15 is a sectional view of said fluidic flow line.

The capillaries 3000, 3001 to convey the gas onto the chip are made of glass and bonded by means of an epoxy adhesive cross-linked at high temperature, for example sold under the name of EPO-TEK® 731, designated by the reference 2002.

The respect of these precautions in the choice of the materials makes it possible to ensure the detector withstands high working temperatures.

Furthermore, given the reduced bulk of the detector and the chromatography column, it is possible to miniaturise the gas analysis system, in order for example to embed it in a transportable device, the diameter of which is ten or so centimetres or more. Furthermore, the low flow rate of vector fluid required to drive along the sample and the low energy consumption for the temperature regulation of the chromatography column and the NEMS detector enable the system to have great autonomy. Thus, the system may be used to conduct analyses in not very accessible places, including in hazardous environments.

For example, the gas analysis system may be inserted into an autonomous and programmable underwater vehicle (for example in a pig) or in a drilling tool, and thus make it possible to implement the analyses described above in situ in oceans and reservoirs.

The integration of an instrumentation within pigs and drilling tools is known for other types of sensors, and will thus not be described in greater detail in the present text.

REFERENCES

[Mile2010] E. Mile, G. Jourdan, I. Bargatin, S. Labarthe, C. Marcoux, P. Andreucci, S. Hentz, C. Kharrat, E. Colinet, L. Duraffourg, In-plane nanoelectromechanical resonators based on silicon nanowire piezoresistive detection, Nanotechnology 21, (2010) 165504

[Bao2007] M. Bao, H. Yang, Squeeze film air damping in MEMS, Sensors and Actuators A 136 (2007) 3-27

EP 2 008 965
WO 2012/034990
WO 2012/034951
WO 2014/053575
EP 2 878 942
WO/2015/097282

The invention claimed is:

1. A method for analysing a sample of hydrocarbons, comprising:
    implementing a gas chromatography separation according to a first controlled temperature profile, to separate the sample into analytes; and
    detecting at least one of said analytes by measurement of a variation of a resonance frequency of at least one resonator of nano-electromechanical system (NEMS) type covered with a functional layer made to vibrate at the resonance frequency thereof, under an effect of an adsorption or desorption of the at least one of said analytes by the functional layer,
    wherein the at least one resonator is subjected to a second controlled temperature profile, lower than the first profile,
    wherein the at least one resonator is encapsulated in a temperature regulated chamber, said chamber comprising a temperature regulating unit configured to make the temperature vary inside the chamber in a controlled manner so as to subject the at least one resonator to the second controlled temperature profile,
    wherein a chromatography column used in the gas chromatography separation is encapsulated in a chamber thermally decoupled from the chamber in which the at least one resonator is encapsulated.

2. The method according to claim 1, wherein a temperature difference between the first profile and the second profile is comprised between 5 and 150° C.

3. The method according to claim 1, wherein a temperature of the first profile evolves between 50 and 400° C.

4. The method according to claim 1, wherein the temperature of the second profile evolves between 0 and 350° C.

5. The method according to claim 1, wherein detecting the at least one of said analytes further comprises measuring a variation of a resonance amplitude of the at least one resonator.

6. The method according to claim 5, wherein a molecular composition of the at least one of said analytes is deduced from the measurement of the variation of the resonance frequency of the at least one resonator.

7. The method according to claim 6, wherein a fluidic characteristic of the at least one of said analytes is further deduced from the measurement of the variation of the resonance amplitude of the at least one resonator.

8. The method according to claim 1, wherein the sample comprises carbon chains having between 16 and 40 carbon atoms.

9. The method according to claim 1, further comprising analyzing said at least one of said analytes by a catharometer arranged in a same fluidic conduit as the at least one resonator.

10. The method according to claim 1, further comprising implementing a processing to subtract a base line of a blank response of the at least one resonator measured in the absence of circulation of a fluid at the second controlled temperature profile from a base line of a response of the at least one resonator when exposed to the at least one of said analytes at the second controlled temperature profile.

11. The method according to claim 1, further comprising measuring a variation of a resonance frequency of at least one second resonator, called reference resonator, subjected to the same second temperature profile as the at least one resonator but not exposed to the at least one of said analytes, and implementing a processing configured to subtract from a response signal of the at least one resonator exposed to the at least one of said analytes a response signal of the reference resonator.

12. A method for comparing two petroleum fractions, wherein the method according to claim 1 is implemented to analyse a composition of each of said fractions.

13. A method for assaying a determined compound in a sample of hydrocarbons, wherein the method according to claim 1 is implemented to detect said compound within the sample of hydrocarbons.

14. A method for assaying a determined hydrocarbon in water, wherein the method according to claim 1 is implemented to detect said hydrocarbon within a water sample.

15. A drilling tool or autonomous vehicle for an exploitation of hydrocarbons and/or underwater exploration, comprising an analysis system for implementing the method according to claim 1, said system comprising:
- a gas chromatography column, arranged in a first temperature controlled chamber,
- a resonator of nano-electromechanical system (NEMS) type arranged in a fluidic conduit at an outlet of the chromatography column, said resonator comprising a functional layer, the fluidic conduit being arranged in a second temperature controlled chamber, and
- a reading device suited to make the resonator vibrate at the resonance frequency thereof and to measure a variation of said resonance frequency under the effect of the adsorption or the desorption of the at least one of said analytes by the functional layer,
- the first and the second chambers being thermally decoupled from each other, each chamber comprising a temperature regulating unit, said regulating units being configured to vary the temperature in their respective chamber according to the first controlled temperature profile and to the second controlled temperature profile, respectively.

16. The tool or vehicle according to claim 15, wherein the analysis system further comprises a catharometer arranged in the fluidic conduit, upstream or downstream of the resonator.

17. The tool according to claim 15, wherein the regulating unit of the second chamber comprise a heating element arranged inside the second chamber, and an active cooling system.

18. The method according to claim 1, wherein a temperature difference between the first profile and the second profile is comprised between 30 and 100° C.

19. The method according to claim 1, wherein a temperature difference between the first profile and the second profile is comprised between 40 and 60° C.

20. The method according to claim 1, wherein said regulating unit comprises: a heating element arranged inside the chamber in which the at least one resonator is encapsulated, and an active cooling system.

* * * * *